United States Patent
Hata et al.

(10) Patent No.: US 11,390,842 B2
(45) Date of Patent: Jul. 19, 2022

(54) CELL CULTURE METHOD AND CELL CULTURE APPARATUS

(71) Applicant: TOYO SEIKAN GROUP HOLDINGS, LTD., Tokyo (JP)

(72) Inventors: Norihiko Hata, Tokyo (JP); Masahiro Murai, Tokyo (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 111 days.

(21) Appl. No.: 16/904,690

(22) Filed: Jun. 18, 2020

(65) Prior Publication Data

US 2020/0318057 A1 Oct. 8, 2020

Related U.S. Application Data

(62) Division of application No. 15/542,978, filed as application No. PCT/JP2016/000002 on Jan. 4, 2016, now Pat. No. 10,731,122.

(30) Foreign Application Priority Data

Jan. 30, 2015 (JP) .................................. 2015-017823
Jan. 30, 2015 (JP) .................................. 2015-017824
Jan. 30, 2015 (JP) .................................. 2015-017827

(51) Int. Cl.
*C12M 1/42* (2006.01)
*C12M 1/00* (2006.01)
(Continued)

(52) U.S. Cl.
CPC ............ *C12M 35/04* (2013.01); *C12M 23/26* (2013.01); *C12M 23/34* (2013.01); *C12M 25/06* (2013.01);
(Continued)

(58) Field of Classification Search
CPC ...... C12M 35/04; C12M 23/26; C12M 23/34; C12M 25/06; C12M 29/10; C12N 1/00;
(Continued)

(56) References Cited

U.S. PATENT DOCUMENTS 5,017,490 A 5/1991 Taiariol et al.
5,057,429 A 10/1991 Watanabe et al.
(Continued)

FOREIGN PATENT DOCUMENTS

JP 63-155399 U 10/1988
JP 64-18433 A 1/1989
(Continued)

OTHER PUBLICATIONS

International Search Report dated Feb. 2, 2016, issued by the International Searching Authority in International application No. PCT/JP2016/000002.
(Continued)

*Primary Examiner* — Jennifer M. H. Tichy
(74) *Attorney, Agent, or Firm* — Sughrue Mion, PLLC

(57) ABSTRACT

A cell culture apparatus for conducting cell culture in which a culture medium is supplied together with cells to a container formed of a flexible material, wherein, a base having a flat mounting surface that holds the container is provided, partition pieces that can be protruded from the mounting surface for a prescribed height are embedded in the base, and when the partition pieces are accommodated into the base, upper end surfaces of the partition pieces are flushed with the mounting surface.

11 Claims, 13 Drawing Sheets

(51) Int. Cl.
*C12N 1/00* (2006.01)
*C12N 5/00* (2006.01)
*C12M 1/12* (2006.01)
*C12N 5/071* (2010.01)
*C12N 5/078* (2010.01)
*C12N 5/0775* (2010.01)
*C12N 5/074* (2010.01)

(52) U.S. Cl.
CPC .............. *C12M 29/10* (2013.01); *C12N 1/00* (2013.01); *C12N 5/00* (2013.01); *C12N 5/0625* (2013.01); *C12N 5/0634* (2013.01); *C12N 5/0662* (2013.01); *C12N 5/0696* (2013.01); *C12N 2501/20* (2013.01)

(58) Field of Classification Search
CPC ........ C12N 5/00; C12N 5/0625; C12N 5/634; C12N 5/0662; C12N 5/0696; C12N 2501/20
USPC .................................................. 435/395, 325
See application file for complete search history.

(56) References Cited

U.S. PATENT DOCUMENTS

| | | |
|---|---|---|
| 5,071,760 A | 12/1991 | Watanabe et al. |
| 9,388,376 B2 | 7/2016 | Suenaga et al. |
| 2004/0214313 A1 | 10/2004 | Zhang et al. |
| 2009/0170714 A1 | 7/2009 | Shimamoto |
| 2010/0075406 A1 | 3/2010 | Tanaka et al. |
| 2010/0203624 A1 | 8/2010 | Singh |
| 2011/0230855 A1 | 9/2011 | Hirabuki |
| 2011/0238029 A1 | 9/2011 | Biset et al. |
| 2011/0318725 A1 | 12/2011 | Suenaga et al. |
| 2013/0164831 A1 | 6/2013 | Tanaka et al. |
| 2013/0244322 A1 | 9/2013 | Henon et al. |
| 2014/0011186 A1 | 1/2014 | Suenaga et al. |
| 2014/0302597 A1 | 10/2014 | Zhou et al. |
| 2015/0209495 A1 | 7/2015 | Biset et al. |
| 2015/0209496 A1 | 7/2015 | Biset et al. |
| 2017/0015965 A1 | 1/2017 | Hata |
| 2017/0073626 A1 | 3/2017 | Hata |

FOREIGN PATENT DOCUMENTS

| | | |
|---|---|---|
| JP | 3-505164 A | 11/1991 |
| JP | 2000-125848 A | 5/2000 |
| JP | 2004-89136 A | 3/2004 |
| JP | 2006-325437 A | 12/2006 |
| JP | 2011-109933 A | 6/2011 |
| JP | 2011-239734 A | 12/2011 |
| JP | 2011-241159 A | 12/2011 |
| JP | 2012-510298 A | 5/2012 |
| JP | 2012-510299 A | 5/2012 |
| JP | 2012-239401 A | 12/2012 |
| JP | 5265687 B2 | 8/2013 |
| JP | 2013-215141 A | 10/2013 |
| JP | 2015-188390 A | 11/2015 |
| JP | 2015-188391 A | 11/2015 |
| KR | 10-2013-0031897 A | 3/2013 |
| WO | 2007/122814 A1 | 11/2007 |
| WO | 2008/136371 A1 | 11/2008 |
| WO | 2009/123173 A1 | 10/2009 |
| WO | 2012/032761 A1 | 3/2012 |
| WO | 2013/088537 A1 | 6/2013 |
| WO | 2015/133116 A1 | 9/2015 |
| WO | 2015/145954 A1 | 10/2015 |

OTHER PUBLICATIONS

Office Action dated Jun. 11, 2019 for corresponding Japanese Patent Application No. 2015-017827.
International Preliminary Report on Patentability dated Aug. 1, 2017, issued by the International Bureau in International application No. PCT/JP2016/000002.

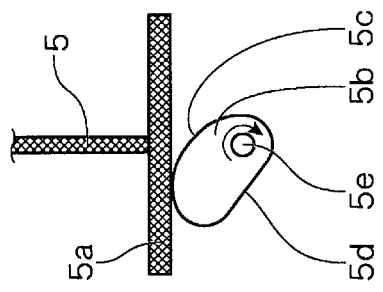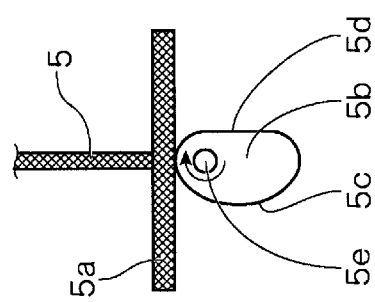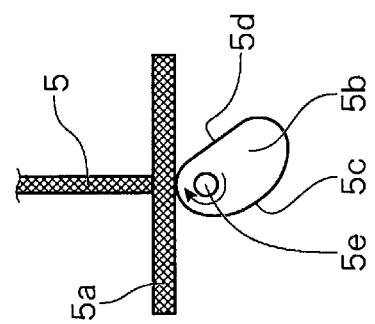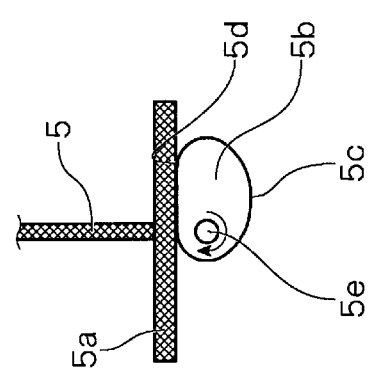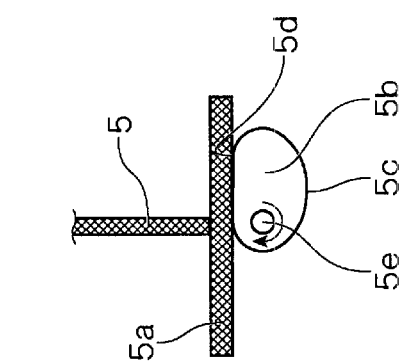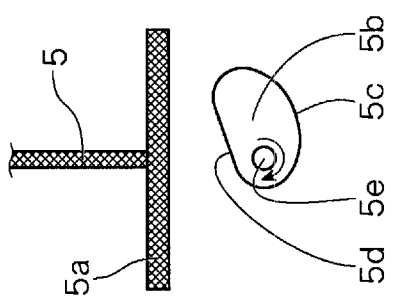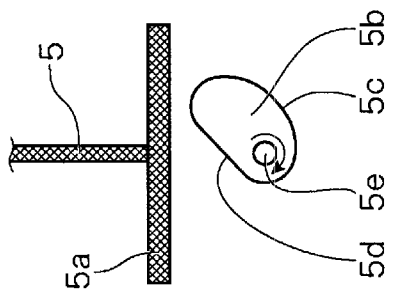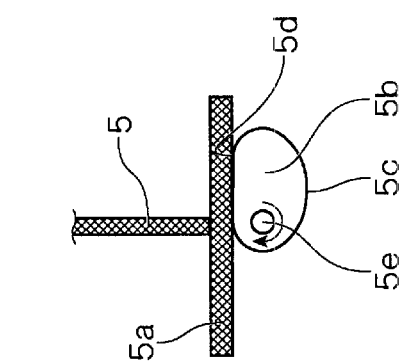

CELL CULTURE METHOD AND CELL CULTURE APPARATUS

CROSS REFERENCE PARAGRAPH

This is a divisional application of U.S. application Ser. No. 15/542,978 filed Jul. 12, 2017, which is a National Stage of International Application No. PCT/JP2016/000002, filed Jan. 4, 2016, claiming priority based on Japanese Patent Application No. 2015-017823 filed Jan. 30, 2015, Japanese Patent Application No. 2015-017824 filed Jan. 30, 2015 and Japanese Patent Application No. 2015-017827 filed Jan. 30, 2015, the contents of all of which are incorporated herein by reference in their entirety.

TECHNICAL FIELD

The present invention relates to a cell culture method for culturing cells under an artificial environment and a cell culture apparatus.

BACKGROUND ART

In recent years, in the field of production of medicines, gene therapy, regenerative therapy, immunotherapy and the like, it is required to culture cells, tissues, microorganisms, viruses, etc. (these are collectively referred to as "cells") efficiently in a large amount in an artificial environment. In such cell culture, as the cell density in a culture solution (hereinafter the culture solution means one including cells and a culture medium) increases, depletion of culture medium components necessary for proliferation, and accumulation of metabolic products of the cells themselves occur, the proliferation rate decreases and the cell density reaches saturation. Therefore, when cells are cultured in a relatively large amount, culture is usually carried out while repeating subculture so that the cell density is maintained properly.

At the time of subculture, there may be cases where cells are transferred from a well plate to a flask, etc. For example, using cell culture well plates, cells are added to individual wells together with a culture medium so as to attain a proper cell density, and culture is started. After sufficiently proliferating the cells in the wells, the proliferated cells are transferred to a cell culture flask. In accordance with the progress of cell proliferation, a culture medium is added to conduct culture and also conduct subculture. When the cells are proliferated to a prescribed level, the cells are transferred to a flask or a bag having a larger capacity, and culture, supplement of a culture medium, and subculture are repeated, whereby the cells are cultured in a large amount (see paragraph [0027], etc. of Patent Document 1).

Also, a method as following is adopted when using cryopreserved cells. After thawing, culture is conducted for several days in a high density state using a well plate in order to restore the original functions of the cells (hereinafter referred to as "curing culture"), and after restoring the function of the cells to their original state, the cells are transferred to a flask and cultured (hereinafter referred to as "expansion culture"), followed by activation culture in which antibody stimulation is performed is conducted (see paragraph [0057], etc. of Patent Document 2).

In such cell culture, equipment such as a well plate or a flask has been conventionally used, but in recent years, in place of these equipment, a culture bag made of a flexible material such as a resin film has come to be used (see Patent Documents 3 and 4). Equipment such as a well plate and a flask is not suited to culture a large amount of cells. On the contrary, in the case of using a culture bag, not only the cells can be cultured in a large amount since the capacity of the bag can be increased easily, but also cell culture can be conducted in a closed system, and hence, it has a merit that risk of contamination by fungi or virus during culture can be reduced. Therefore, when the cells are cultured in a large amount on a relatively large scale (i.e. larger than the laboratory scale), a culture bag is preferably used.

RELATED ART DOCUMENT

Patent Documents

Patent Document 1: JP-A-2011-241159
Patent Document 2: JP-A-2013-215141
Patent Document 3: WO2012/032761
Patent Document 4: WO2008/136371

DISCLOSURE OF THE INVENTION

Problems to be Solved by the Invention

However, in such cell culture, it is necessary to repeat pipetting operation many times when transferring the cells from a well plate to a flask, and every time subculture is conducted, the cells are required to be transferred to a new culture container such as a flask and a bag, not only an operation becomes complicated, but also the cells may be damaged. Further, there is a high risk of contamination.

The present invention has been attained taking the above-mentioned circumstances into consideration, and an object thereof is to provide a cell culture method and a cell culture apparatus capable of maintaining the cell density at the time of culture at an appropriate level, and also capable of eliminating the need of a task of transfer of cells from one culture container to another when proliferating a large amount of cells, thereby to reduce damage on cells and lower risk of contamination.

Means for Solving the Problems

The cell culture method according to the present invention is a method of culturing cells in which a culture medium is supplied together with cells to a container formed of a flexible material, thereby to conduct cell culture, wherein,
a bottom surface of the container is partially raised to be partitioned into a plurality of compartments,
the cells are cultured in each compartment, and
in due time, the compartments are removed to expand a culture area in the container.

Further, the cell culture apparatus according to the present invention is a cell culture apparatus for conducting cell culture in which a culture medium is supplied together with cells to a container formed of a flexible material, wherein,
a base having a flat mounting surface that holds the container is provided,
partition pieces that can be protruded from the mounting surface for a prescribed height are embedded in the base, and
when the partition pieces are accommodated into the base, upper end surfaces of the partition pieces are flushed with the mounting surface.

Advantageous Effects of the Invention

According to the present invention, while culturing cells in a state where the cell density is increased, by expanding the culture area in the container when the density of proliferated cells is increased to a level exceeding a level suited to culture, it becomes possible to proliferate cells efficiently while maintaining the cell density at an appropriate level without conducting subculture.

Further, since transfer of cells from one culture container to another is not necessary, and a culture solution is retained in the same culture container, reduction of damage on cells and reduction of risk of contamination become possible.

BRIEF DESCRIPTION OF THE DRAWINGS

FIGS. 10A to 10H are explanatory views showing one example of a driving mechanism that moves up and down a push-up member that rotates a base provided in the cell culture apparatus shown in FIG. 3;

MODE FOR CARRYING OUT THE INVENTION

Hereinbelow, preferred embodiments of the present invention will be explained with reference to the drawings.
[Cell Culture Method]
First, the cell culture method according to the present embodiment will be explained.

The cell culture method according to the present embodiment is a cell culture method in which cells to be cultured (cultured cells) C and a culture medium M to culture these cells C are supplied to a container 1 formed of a flexible material, thereby to conduct cell culture. In particular, the cell culture method is suitable for culturing damaged cells, such as cells that have been sampled from a patient or cells that have been frozen, while curing them and recovering the functions inherent to them.

In the present embodiment, the container 1 is formed of a flexible material and formed into a bag-like shape. The shape is normally rectangular in many cases. For example, it may be a bag of which the four sides are sealed by heat sealing, or may be an integrally-shaped bag obtained by blow molding.

The container 1 may be in a square shape, an elliptical shape, a circular shape, or the like, and may have various shapes according to need.

Further, it is preferred that the container 1 be capable of conducting cell culture in a closed system (sealed system) and have permeability to oxygen and carbon dioxide that is required when the container is used in a $CO_2$ incubator. In particular, it is preferred that the container 1 be suited to be used under culture environment of 37° C. and 5% carbon dioxide concentration.

Further, it is preferred that part or all of the container 1 have transparency such that the progress situation of cell culture, the state of cells, etc. can be confirmed, and that the container 1 have low cell toxicity, low elution properties, and suitability to radiation sterilization.

As the specific examples of the material of the container 1 that satisfies such conditions, a polyethylene-based resin such as polyethylene, a copolymer of ethylene and α-olefin, a copolymer of ethylene and vinyl acetate, an ionomer obtained by using a copolymer of ethylene and acrylic acid or methacrylic acid and a metal ion, or the like can be given. Further, polyolefin, a styrene-based elastomer, a polyester-based thermoplastic elastomer, a silicone-based thermoplastic elastomer, a silicone resin or the like can also be used.

Figure 5:
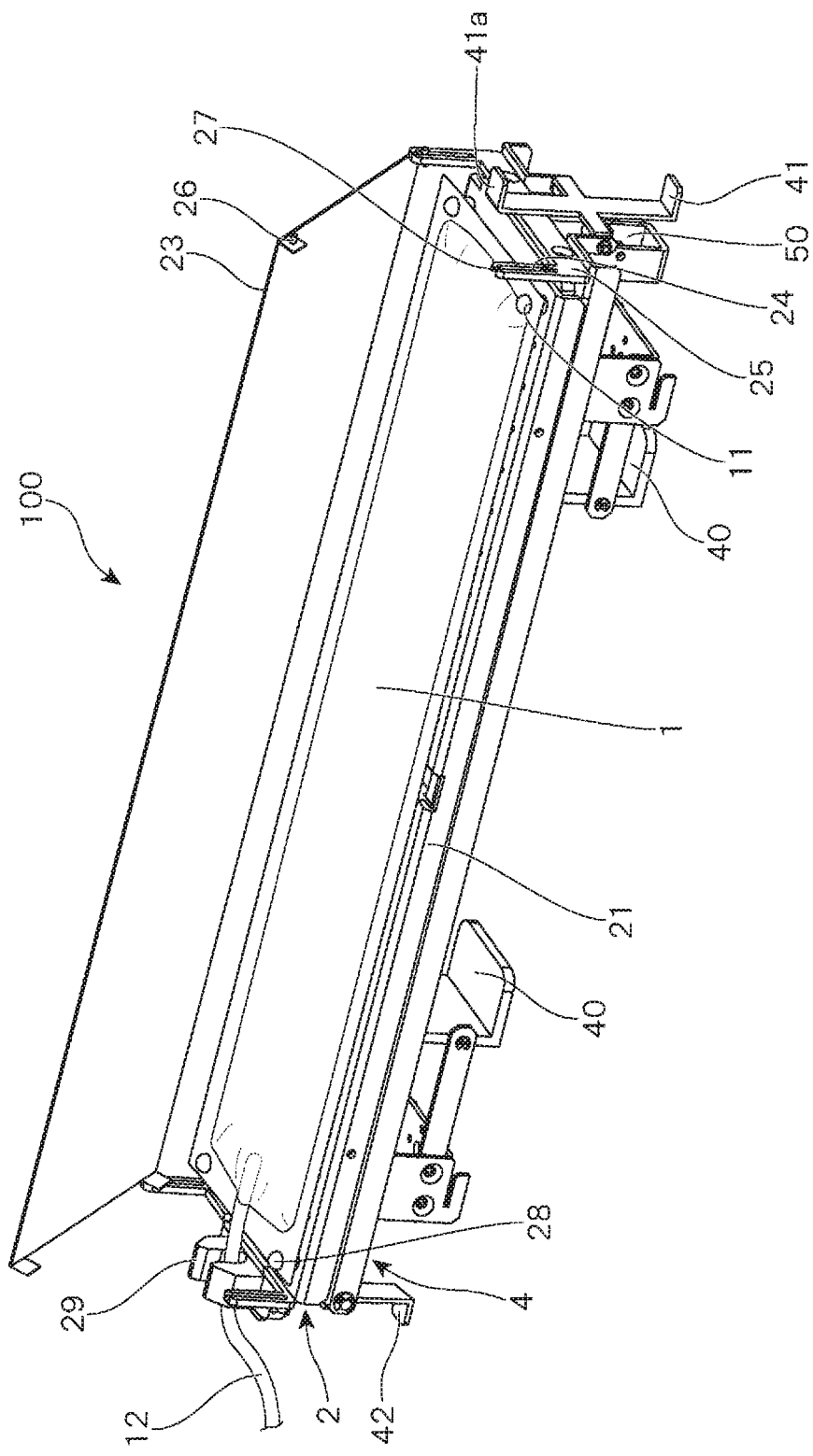
FIG. 5 is a perspective view showing a state in which a mounting surface of the cell culture apparatus shown in FIG. 3 is open.

In the example shown in FIG. 5, a tube 12 is connected to one side of the shorter sides of the container 1 that has a rectangular shape. Through this tube 12, cells or a culture medium are supplied from the outside to the container 1, and after the step in the container 1 is completed, the cells or the culture medium are collected from the container 1. Two tubes may be connected, i.e. one is used for supply and the other is used for collection. In addition to these tubes, a tube for taking out a sample or other tubes may be connected.

Although not particularly shown, the tube 12 may be connected to a tubular port attached to the container 1. In order to reduce the amount of a remaining liquid when cells or a culture medium are collected from the container 1, the container 1 may be configured such that the accommodation part thereof has a shape that becomes gradually narrow toward the port.

The material of the tube 12 connected to the container 1 may be appropriately selected according to the environment of use. When the container is used in a $CO_2$ incubator, it is desirable to use one having excellent gas permeability for oxygen and carbon dioxide. When the container is used outside a $CO_2$ incubator, it is desirable to use one having gas barrier properties.

Specifically, silicone rubber, soft vinyl chloride resins, polybutadiene resins, ethylene-vinyl acetate copolymers, chlorinated polyethylene resins, polyurethane-based thermoplastic elastomers, polyester-based thermoplastic elastomers, silicone-based thermoplastic elastomers, styrene-based elastomers or the like can be used. As the styrene-based elastomer, SBS (styrene-butadiene-styrene), SIS (styrene-isoprene-styrene), SEBS (styrene-ethylene-butylene-styrene), SEPS (styrene-ethylene-propylene-styrene) or the like can be used.

The cell culture method according to the present embodiment cultures, using such container 1, the cells that have suffered damage and whose functions have declined, such as cells that have been sampled from a patient or cells that have been thawed after frozen storage. Also it comprises a curing culture step in which such damaged cells are cultured while curing at the initial stage of cell culture in order to recover the functions inherent to the cells, and an expansion culture step in which, after curing of the cells proceeds to some extent, the culture area in the container is expanded and culture of cells is continued until a prescribed cell density is attained.

Figure 1:
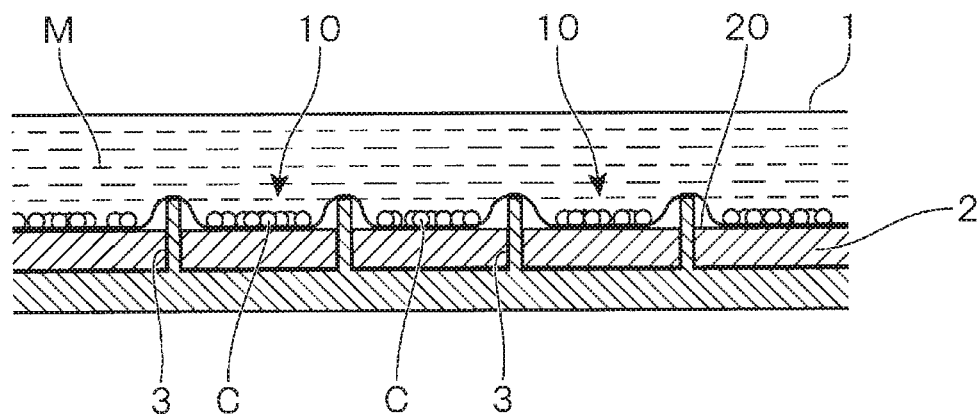
FIG. 1 is an explanatory view showing an outline of the curing culture step in the cell culture method according to the embodiment of the present invention.

In the present embodiment, in the curing culture step, as shown in FIG. 1, the container 1 in which the culture medium M is supplied together with the cells C is held on a base 2 having a flat mounting surface 20. The bottom surface of the container 1 is partially raised by partition pieces 3 that protrude from the mounting surface 20 for a prescribed height, thereby to partition it into a plurality of compartments 10. The cells C are cultured in each compartment 10. At this time, in the bottom surface of the container 1, parts deformed by pushing up of the partition pieces 3 are raised from the mounting surface 20 as if they float up, and the remaining flat parts that contact the mounting surface 20 serve as a culture surface.

As a result, when cells C are supplied to the container 1 in a state that they are suspended in the culture medium M, thereafter, irrespective of being floating cells or anchorage-dependent cells, the cells C are settled to the bottom surface of the container 1. Due to collecting of the settled cells C on the culture surface of each compartment 10, the cells C can be cultured at a high cell density.

As described above, in the curing culture step, the cells C are collected on the culture surface of each compartment 10, and cell culture is conducted. By adjusting the number, interval, size, etc. of the compartments 10 formed on the bottom surface of the container 1, it is possible to adjust the density of the cells C collected on the culture surface of each compartment 10 to an appropriate range.

It is preferred that the area of the culture surface in each compartment 10 be almost the same as the bottom surface area of each well of a well plate (e.g. 24-well plate, etc.) that has been conventionally used for subculture in accordance with the type or inoculation concentration of cells C to be cultured.

When conducting a curing culture step in the manner mentioned above, the partition piece 3 that partitions the bottom part of the container 1 is formed in a rectangular shape with a prescribed thickness. The thickness or the protrusion height from the mounting surface 20 are appropriately set in order to prevent cells during culture from moving across the compartments. For example, the thickness of the partition piece 3 is preferably 0.5 to 2.0 mm, and the protrusion height from the mounting surface 20 is preferably 0.5 to 1.5 mm.

Subsequently, in the curing culture step, the cells C are cultured in each compartment 10 formed on the bottom surface of the container 1 in a state where the cell density is increased, and after the density of the proliferated cells C (the number of cells per unit area of the culture surface of each compartment 10) is increased to a level equal to or higher than a prescribed level, the curing culture step shifts to the expansion culture step.

Figure 2:
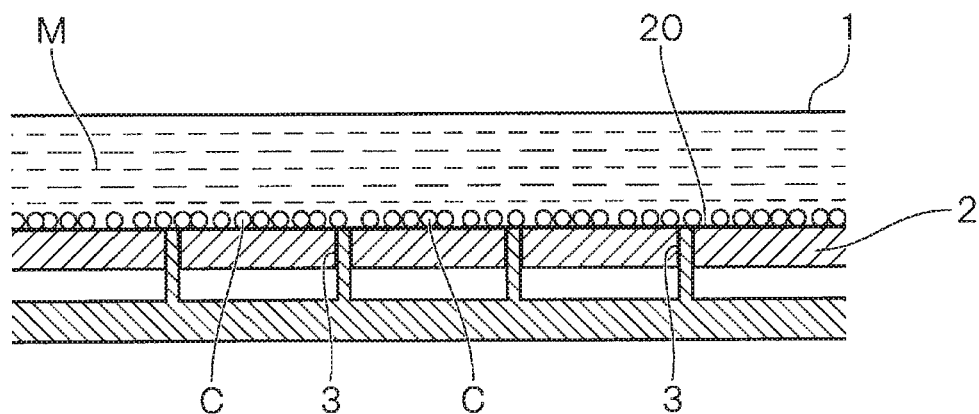
FIG. 2 is an explanatory view showing an outline of the expansion culture step in the cell culture method according to the embodiment of the present invention.

In the expansion culture step, as shown in FIG. 2, the partition pieces 3 are accommodated into the base 2, and the upper end surfaces of the partition pieces 3 are flushed with the mounting surface 20, thereby to remove the compartments 10, and to allow the container 1 to be used as one compartment. As a result, the culture area is expanded.

That is, as mentioned above, in the curing culture step, on the bottom surface of the container 1, parts that are deformed by pushing up of the partition pieces 3 are raised as if they float up from the mounting surface 20, whereby the bottom surface is partitioned into plural compartments 10. By accommodating the partition pieces 3 into the base 2 and allowing the upper surfaces thereof to be flushed with the mounting surface 20 to remove the compartments 10, the parts are flattened by the weight of the content liquid and can be used as a culture surface, and as a result, the culture area is expanded in an amount corresponding to the amount of the flattened parts.

As mentioned above, in the present embodiment, the cells C are cultured while curing in the curing culture step in a state where the cell density is increased. When the density of the proliferated cells C is increased to a level equal to or higher than a certain level and exceeds a range that is suited to culture, the curing culture step shifts to the expansion culture step, whereby the culture area in the container is expanded, and culture of cells C is continued until a prescribed cell density is attained. When continuing cell culture by expanding the culture area in the container, a culture medium M is additionally supplied to the container 1 according to need.

When shifting to the expansion culture step, it is preferred that the content liquid in the container 1 be stirred. For example, after moving the container 1 to a position higher than the initial position, the container 1 is returned to the initial position, and vibration is applied to the container 1 that is returned to the initial position. By repeating this operation, the content liquid in the container 1 can be stirred.

By doing so, in addition to the stirring of the content liquid by the up-and-down movement of the container 1, the cells C are diffused as if they fly up in the content liquid by vibration applied to the container 1. As a result, not only the content liquid in the container 1 is stirred efficiently in the up-and-down direction, the distribution of the cells C in the content liquid or the concentration of the culture medium M in the container 1 can be uniform to maintain good culture environment, but also adhesion to the inner wall of the container or excessive aggregation of the cells C can be suppressed, whereby proliferation of the cells C can be promoted. Further, when the cells C to be cultured are adherent cells, by vibration applied to the container 1, it is possible to promote peeling of the cells C from the culture surface of the container 1.

By the cell culture method according to the present embodiment, not only the cells C can be proliferated efficiently while maintaining the cell density at the time of culture at an appropriate level without conducting subculture, but also transfer of cells from one culture container to another culture container becomes unnecessary. Due to retention of the culture solution in the same culture container, damage on the cells C and risk of contamination can be reduced.

Therefore, in the case of culturing floating cells such as lymphocytes, for example, by applying the present embodiment, the cells C are collected in each compartment 10 formed on the bottom surface of the container 1, the concentration of activator substances such as cytokine generated by the cells C is locally increased, and the interaction between the cells occurs, whereby culture can be conducted with an increased cell activity. Subsequently, by expanding the culture area in the container after the cells C are proliferated to some extent, the cells C can be cultured efficiently in the same container while maintaining an appropriate cell density. Therefore, the present embodiment is suitable in particular for culturing efficiently the cells that have suffered damage and whose functions have declined such as cells that just have been sampled from a patient or cells that have just been thawed after frozen storage efficiently, while curing them and recovering the functions inherent to them.

When culturing anchorage-dependent cells such as skin cells, iPS cells, mesenchymal stem cells, for example, by applying the present embodiment, the cells C are adhered to the culture surface of each compartment 10 formed on the bottom surface of the container 1, and proliferated. After that, by removing the compartments 10 to expand the culture area in the container, the culture surface on which the cells C can be proliferated can be expanded with an appropriate arrangement. Therefore, an operation such as subculture, i.e. an operation of collecting cells by peeling them from the culture surface and inoculation of cells to a new culture container, which is an operation that is complicated and has a risk of lowering proliferation efficiency, becomes unnecessary, whereby cell culture can be conducted in the same container under similar culture environment to that of subculture.

In the meantime, the container 1 used in the present embodiment is easily deformed since it is formed of a flexible material, and hence, the shape is not stable. Therefore, during the culture period that requires several days in general, if the container 1 is deformed by application of vibration, etc., the content liquid excessively flows to damage the cells, thus lowering the culture efficiency. Taking such circumstances into consideration, in the present embodiment, when cell culture is conducted by supplying the culture medium M together with the cells C to the culture container 1 formed of a flexible material, it is preferred that cell culture be conducted in a state that the inside of the container is pressurized so that the container 1 is not easily deformed when vibration is applied during a long-term culture period and flow of the content liquid that damages the cells C during culture is suppressed, thereby enabling efficient proliferation of the cells C. This will be explained later.

[Cell Culture Apparatus]

Subsequently, an explanation will be made on the cell culture apparatus according to the present embodiment that is preferable to be used in the cell culture method mentioned above.

Figure 3:
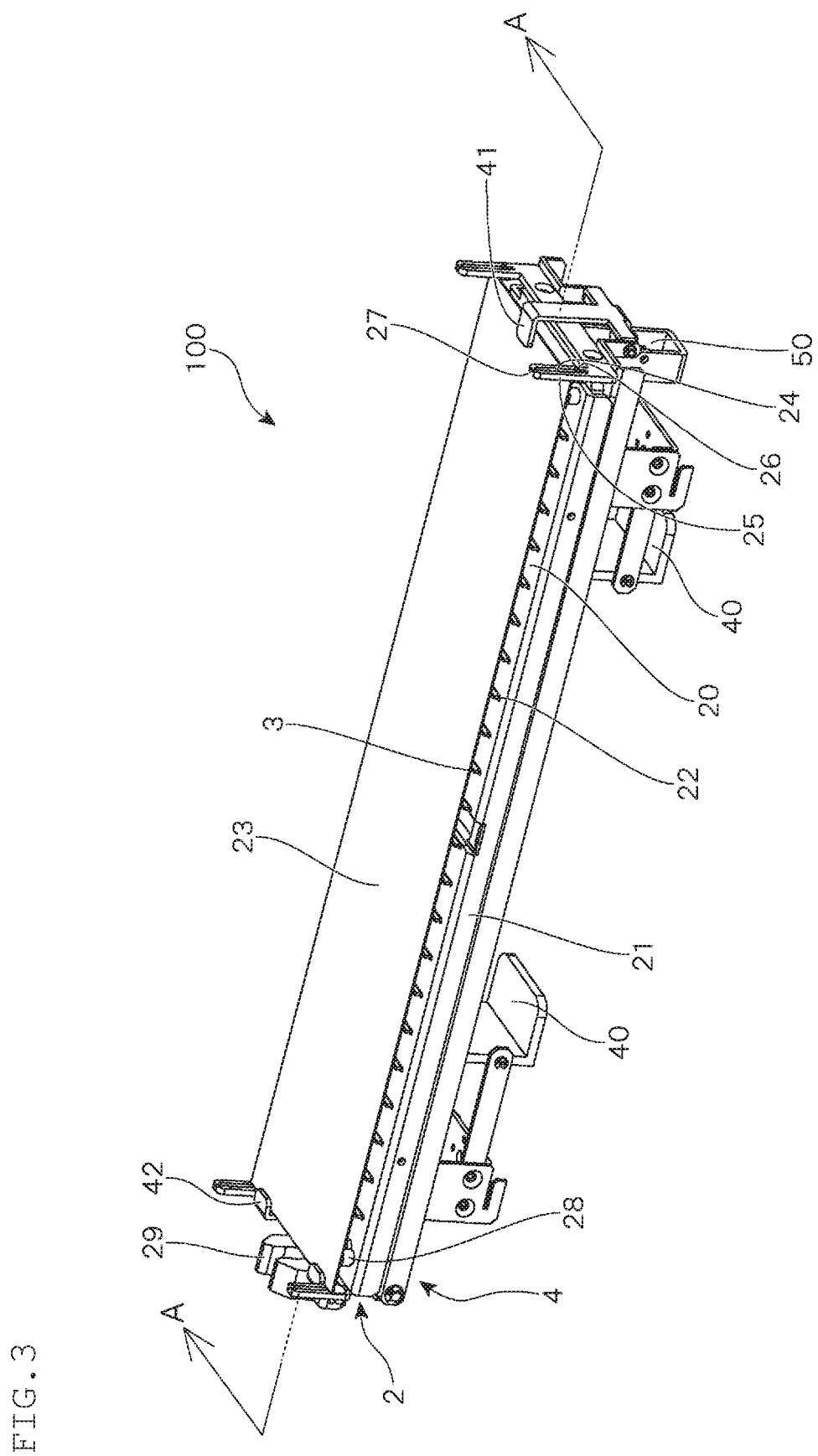
FIG. 3 is a perspective view showing an outline of the cell culture apparatus according to the embodiment of the present invention.

FIG. 3 is a perspective view showing an outline of the cell culture apparatus according to the present embodiment.

In the present embodiment, a culture apparatus 100 is provided with a base 2 having a flat mounting surface 20 for holding the container 1. In such base 2, one end on the shorter sides thereof is pivotally supported by a supporting frame 4, and the base 2 can be rotatably moved around the axis.

In addition, the base 2 includes a holding member 21 that forms the mounting surface 20 and the partition plates 30 that are disposed below the holding member 21, and the partition plates 30 are provided with a plurality of rectangular partition pieces 3 that are vertically arranged in parallel at regular intervals. On the mounting surface 20 of the holding member 21, a plurality of slits 22 are provided in parallel along the longitudinal direction, and the partition pieces 3 arranged vertically on the partition plates 30 can be respectively protruded from the slits 22. Due to such a configuration, the partition pieces 3 that can be protruded from the mounting surface 20 for a prescribed height are embedded in the base 2.

Figure 4:
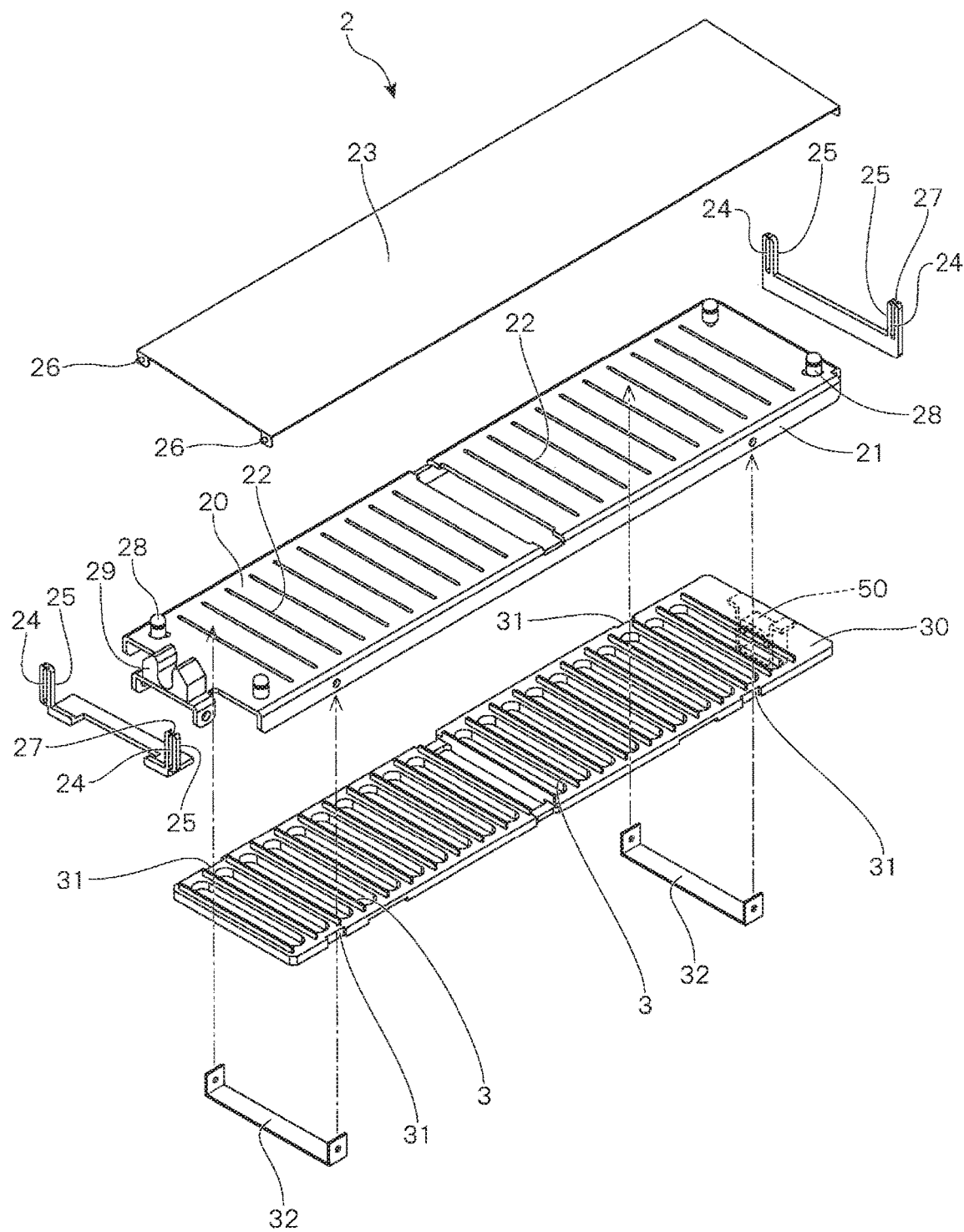
FIG. 4 is an exploded perspective view of a base provided in the cell culture apparatus shown in FIG. 3.

Here, FIG. 4 shows an exploded perspective view of the base 2 that is provided in the culture apparatus 100 shown in FIG. 3. In the present embodiment, on the both side surfaces of the longer sides of the partition plate 30, two pairs of notched parts 31 are formed. These notched parts 31 are obtained by notching the opposing parts of the side surfaces with a prescribed width. By fitting a guide member 32 to the holding member 21 in a state where the two guide members 32 are loosely fitted to these notched parts 31, the partition plate 30 can be positioned below the holding member 21. At this time, the shape, dimension, etc. of each element is appropriately adjusted such that, in the state where the partition plates 30 are floated from the guide member 32 to allow them to be pressed against the holding member 21, the partition pieces 3 are protruded from the mounting surface 20 for a prescribed height and in the state where the partition plates 30 are supported by the guide member 32, the upper surfaces of the partition pieces 3 are flushed with the mounting surface 20 (see FIG. 6 and FIG. 9).

On the other hand, to the supporting frame 4 that pivotally supports the base 2, two supporting members 40 having an L-shaped cross section are rotatably attached with the proximal end of the longer side being pivotably supported. In such supporting member 40, when the longer side is in parallel with the vertical direction, the front end on the longer side thereof contacts the lower surface of the partition plate 30, and as a result, the partition plate 30 is lifted up, and supports the partition plate 30 such that it is pressed against the holding member 21 (see FIG. 6). When the contact with the partition plate 30 is released, the supporting member 40 is rotatably moved such that the longer side thereof is inclined relative to the vertical direction by the weight of the shorter side thereof (see FIG. 7). The partition plate 30 that is no longer supported by the supporting member 40 is lowered to a position at which it is supported by the guide member 32. As a result, the partition pieces 3 are accommodated into the base 2, whereby the upper end surfaces of the partition pieces 3 are flushed with the mounting surface 20.

Further, to the base 2, the pressing plate 23 that presses the upper surface of the container 1 held on the mounting surface 20 to pressurize the inside of the container is attached. The pressing plate 23 can be attached in such a manner that, in order to allow the pressing plate 23 to move up and down in accordance with the amount of the content in the container 1 (see FIG. 11 and FIG. 12), as shown, at each of the four corners of the base 2, an annular rising piece 25 forming an elongated hole-shaped guide hole 24 is vertically provided, and a pin 26 that is horizontally provided in a protruded manner at the four corners of the pressing plate 23 is inserted into the guide hole 24.

Further, in the shown example, among the four annular rising pieces 25 provided in the base 2, at the upper end side of the two annular rising pieces 25 positioned at the both ends on one of the longer sides of the base 2, a thinned part 27 that is formed by notching in a groove-shape is formed. Thereby, when a force is applied in a state where the pin 26 that is inserted into the guide hole 24 of the annular rising piece 25 contacts the upper edge of the guide hole 24 when the pressing plate 23 is lifted up, the pin 26 is removed from the guide hole 24 through the thinned part 27.

Due to such a configuration, as shown in FIG. 5, the mounting surface 20 can be opened by lifting up the pressing plate 23 obliquely. In this state, holes 11 bored at the four corners of the container 1 are engaged with fixtures 28 provided at the four corners of the base 2, and the tube 12 connected to the container 1 is fixed to a tube-fixing member 29, whereby the container 1 can be attached to the culture apparatus 100.

When attaching the container 1 to the culture apparatus 100, to the container 1, the culture medium M is supplied together with the cells C, thereby allowing a prescribed amount of a content liquid to be stored in the container. Then, after attaching the container 1 to the culture apparatus 100, the pressing plate 23 is returned to its initial position to allow it to be pressed against the container 1, and hooks 41 and 42 are engaged with two sides of the shorter sides of the pressing plate 23, whereby the pressing plate 23 can be fixed at a lower position. As a result, the upper surface of the container 1 held on the mounting surface 20 is pressed by the pressing plate 23, whereby the inside of the container is pressurized.

Each of the hooks 41 and 42 to be engaged with the pressing plate 23 is pivotably supported by the supporting frame 4 such that it can be rotatably moved. By moving the hooks 41 and 42 rotatably, engagement with and release from the pressing plate 23 can be conducted. The pressing plate 23 after releasing of the hooks 41 and 42 can be moved upward to a higher position at which the pin 26 contacts the upper edge of the guide hole 24.

Subsequently, the operation of the culture apparatus 100 will be explained.

FIGS. 6 to 9 are each an explanatory view for explaining the operation of the cell culture apparatus according to the present embodiment, and the cross sections shown in these figures correspond to cross sections taken along the line A-A in FIG. 3.

Figure 6:
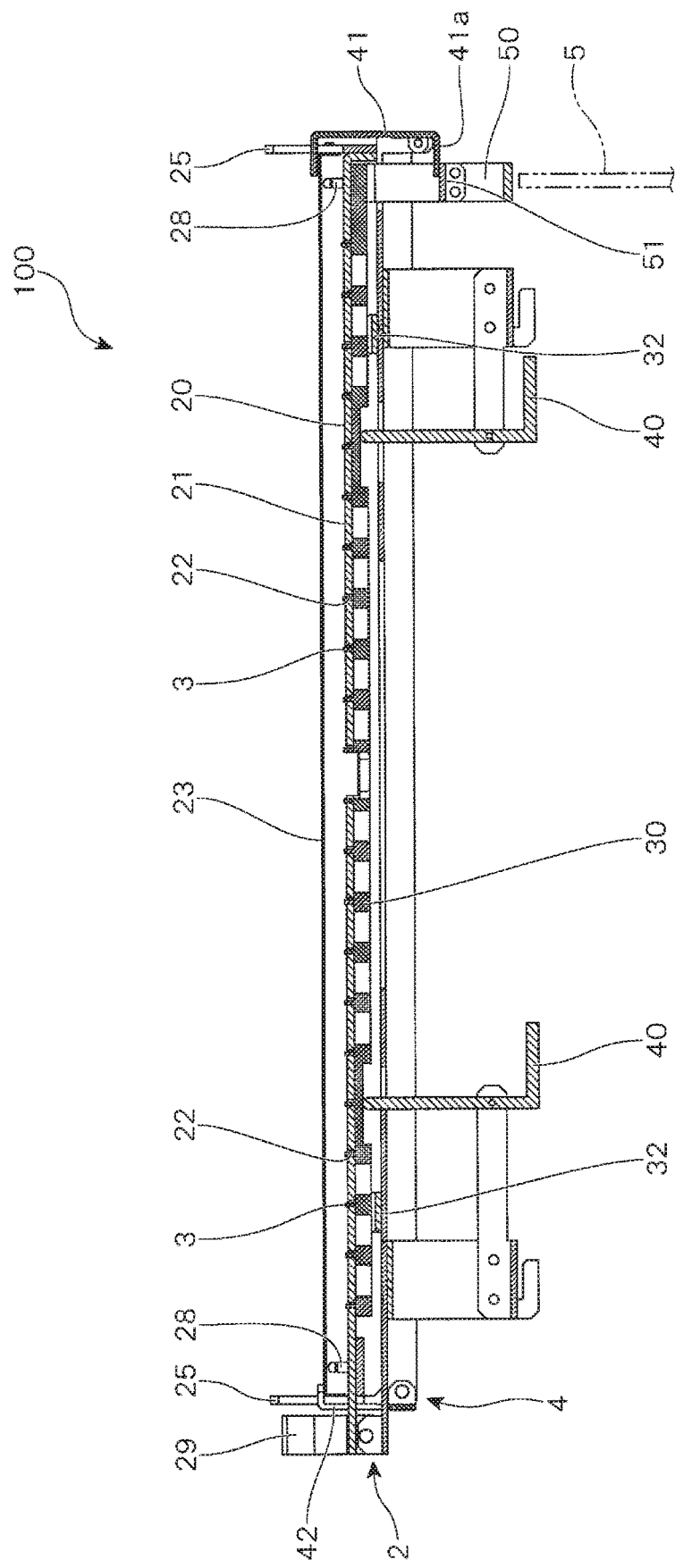
FIG. 6 is an explanatory view for explaining the operation of the cell culture apparatus shown in FIG. 3.

FIG. 6 shows the initial state of the culture apparatus 100. If the container 1 to which the culture medium M is supplied together with the cells C is attached in this state, by the partition pieces 3 that protrude for a prescribed height from the mounting surface 20, the bottom surface of the container 1 is partitioned into a plurality of the compartments 10 (see FIG. 1).

As a result, the curing culture step of the cell culture method mentioned above is ready to start.

Figure 11:
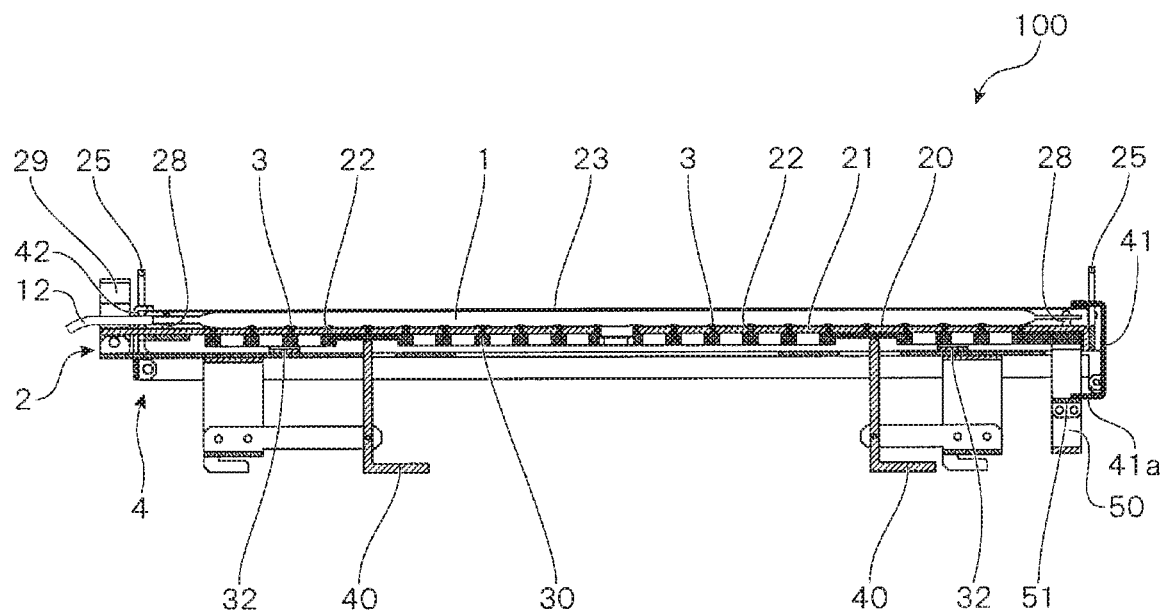
FIG. 11 is an explanatory view showing a state in which a curing culture step is conducted by using the cell culture apparatus shown in FIG. 3.
Figure 12:
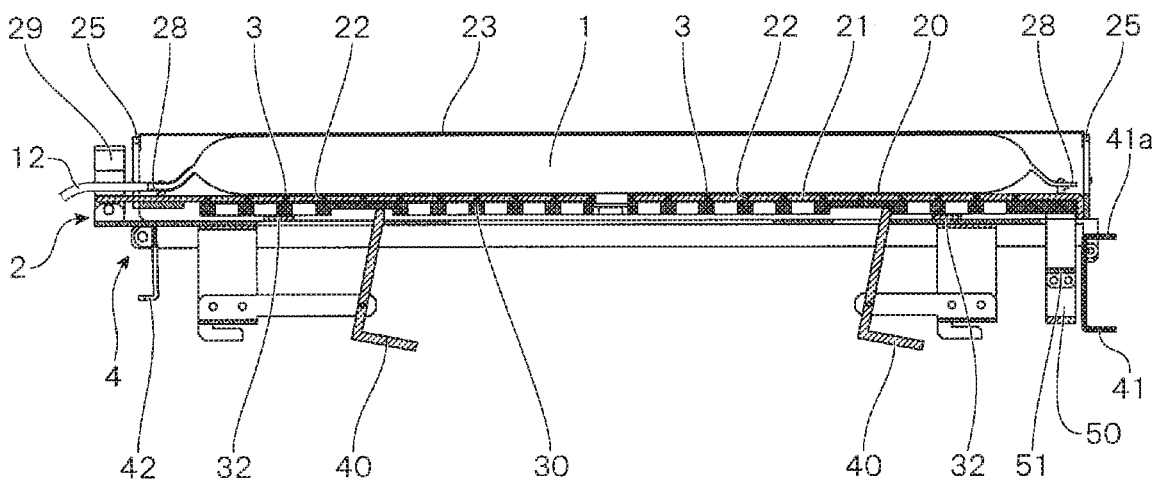
FIG. 12 is an explanatory view showing a state in which an expansion culture step is conducted by using the cell culture apparatus shown in FIG. 3.

In FIGS. 6 to 9, the container 1 is not shown. In the curing culture step, as shown in FIG. 11, the amount of the culture medium M to be supplied to the container 1 is adjusted to be an amount that allows the inside of the container to be pressurized when the upper surface of the container 1 is pressed by the pressing plate 23 fixed at a lower position.

Due to such a configuration, after attaching the container 1 to the culture apparatus 100, the pressing plate 23 is returned to the initial state from the state shown in FIG. 5 and is pressed against the container 1, and the hooks 41 and 42 are engaged with the two sides of the shorter side of the pressing plate 23. As a result, the inside of the container can be pressurized by pressing by means of the pressing plate 23 the upper surface of the container 1 held on the mounting surface 20.

By allowing the inside of the container to be in a pressurized state, excessive flow of the content liquid in the container can be suppressed, so that damage on the cells C during culture can be prevented. Furthermore, if the gas dissolved in the culture medium M evaporates and the bubbles retain in the container, there may be disadvantages that minute bubbles refract the optical path of the illumination when observing the interior of the container, which makes it impossible to observe cells clearly, and that when a gas such as oxygen diffuses from the outside into the culture solution in the container, a gas transfers a boundary of two locations, i.e. the gas and the film and the film and the culture solution, however, due to the retention of bubbles in the container, a gas transfers a boundary of three locations, i.e. the gas and the film, the film and the bubbles, and the bubbles and the culture solution, whereby gas diffusion to the culture solution in the container is lowered. By pressurizing the inside of the container, it is possible to suppress evaporation of a gas dissolved in the culture medium M, whereby the above-mentioned disadvantages can be prevented from occurring.

In the above-mentioned cell culture method, the curing culture step is conducted in the way mentioned above. After the curing culture step proceeds and the density of the cells C that have been proliferated is increased to a level that is equal to or higher than a prescribed level and exceeds a range that is suited to culture, the curing culture step is shifted to an expansion culture step.

Figure 7:
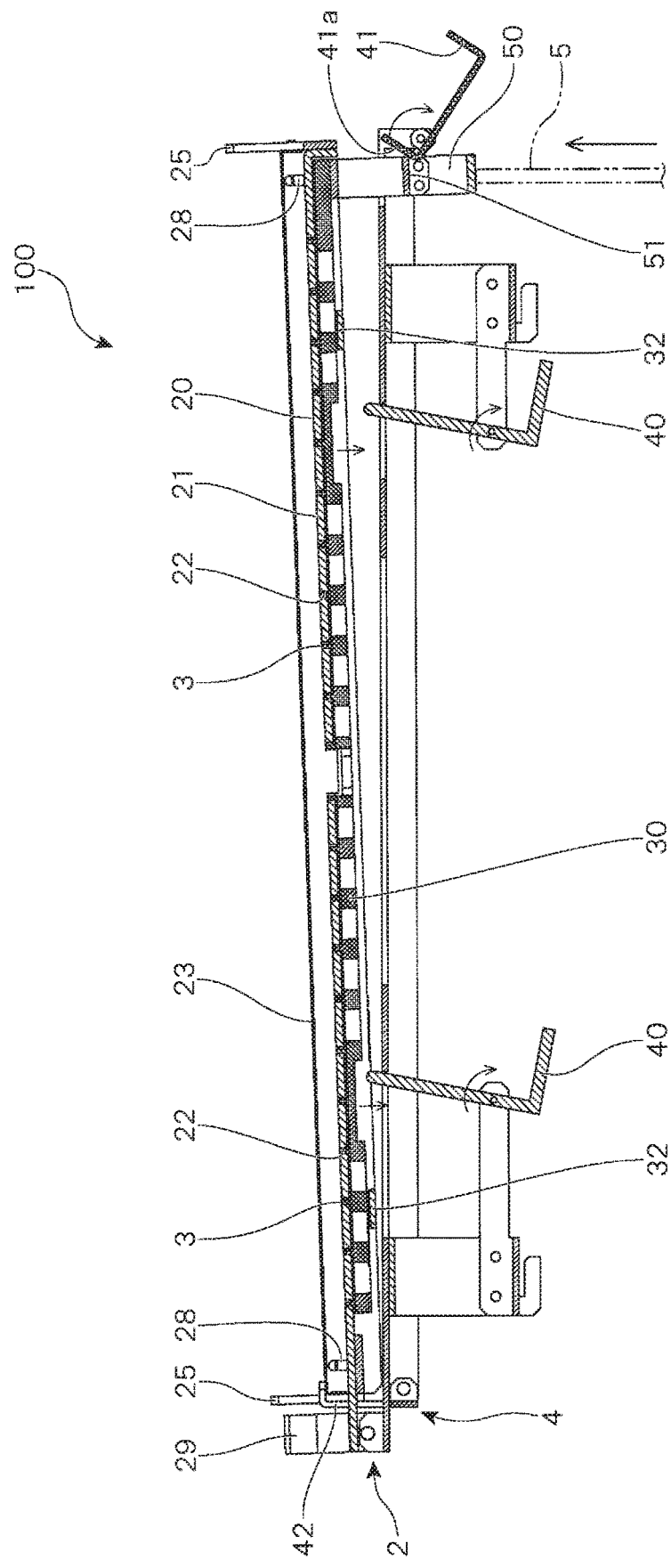
FIG. 7 is an explanatory view for explaining the operation of the cell culture apparatus shown in FIG. 3.

In the present embodiment, when shifting to the expansion culture step, the push-up member 5 moves upward, and the base 2 pivotably supported by the supporting frame 4 is moved upward rotatably around the axis. As a result, as shown in FIG. 7, as for the supporting member 40 that supports the partition plate 30 and has an L-shaped cross section, contact with the partition plate 30 is released, and is rotatably moved by the weight of the shorter side such that the longer side is inclined relative to the vertical direction. The partition plate 30 that is no longer supported by the supporting member 40 is lowered to a position at which it is supported by the guide member 32, and along with this, the partition pieces 3 are accommodated into the base 2, and the upper end surfaces of the partition pieces 3 are flushed with the mounting surface 20. As a result, the compartments 10 formed by division by the partition pieces 3 are removed, and the inside of the container becomes one compartment, whereby the culture area is expanded (see FIG. 2).

Further, in the initial state, the hooks 41 and 42 are engaged with the two sides of the shorter sides of the pressing plate 23. By rotatably moving the base 2 upward, engagement of the hooks 41 and 42 can be released.

Figure 8:
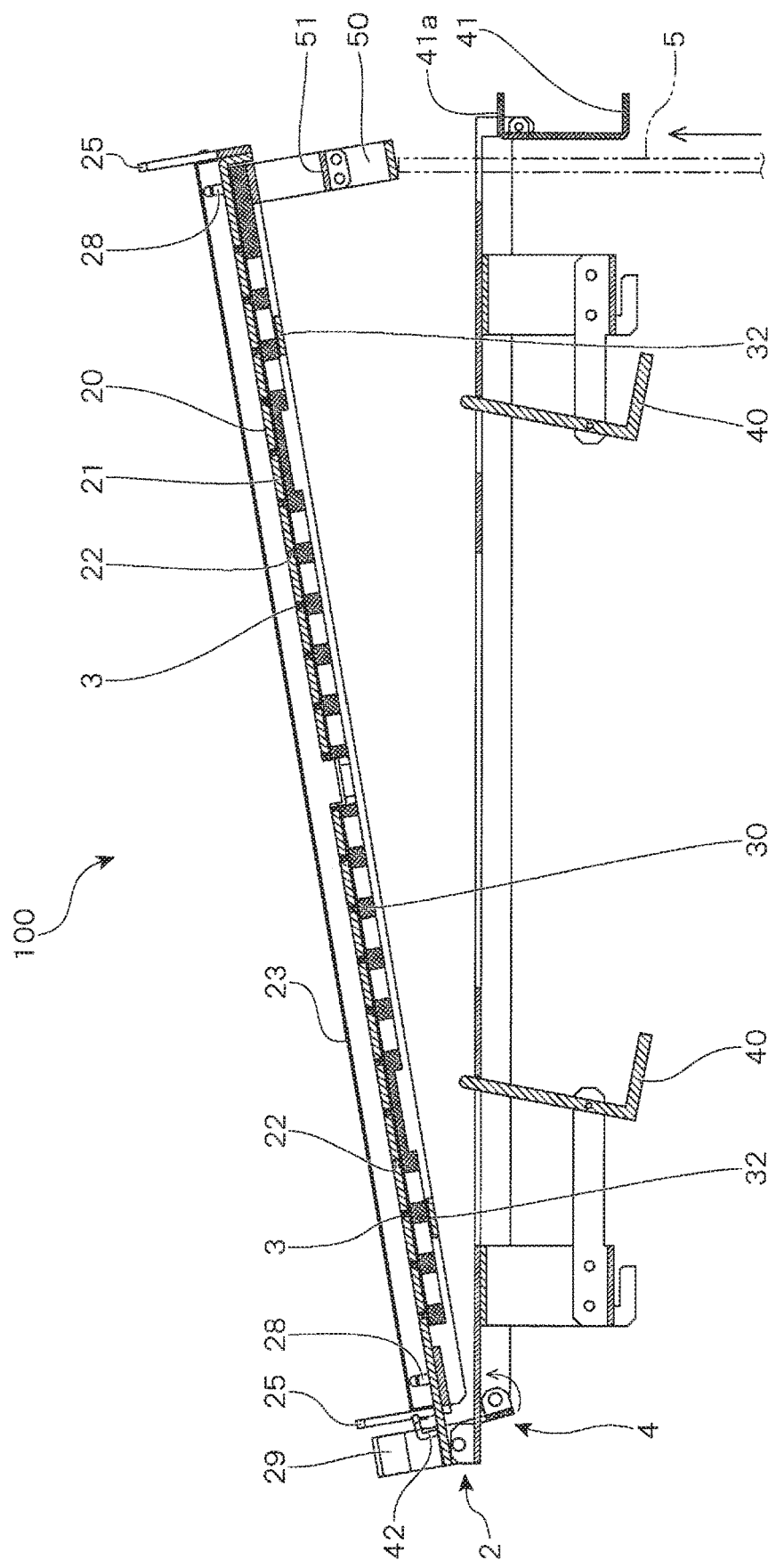
FIG. 8 is an explanatory view for explaining the operation of the cell culture apparatus shown in FIG. 3.

That is, in the present embodiment, the base 2 is rotatably moved upward by allowing the push-up member 5 that has moved upward to contact a contact member 50 provided on the shorter side opposite to the side on which the rotation axis of the base 2 is provided. A beam-like contact piece 51 is bridged over the contact member 50. Then, when the push-up member 5 contacts the contact member 50 to allow the base 2 to move upward rotatably, as shown in FIG. 7, the contact piece 51 contacts a lower tongue piece 41a of the hook 41, that is one of the hooks, then the hook 41 is rotatably moved so that the engagement is released. Then, when the base 2 is further rotatably moved upward, as shown in FIG. 8, the other hook 42 is rotatably moved so as to be pushed by the base 2, and the engagement with the hook 42 is also released.

Figure 9:
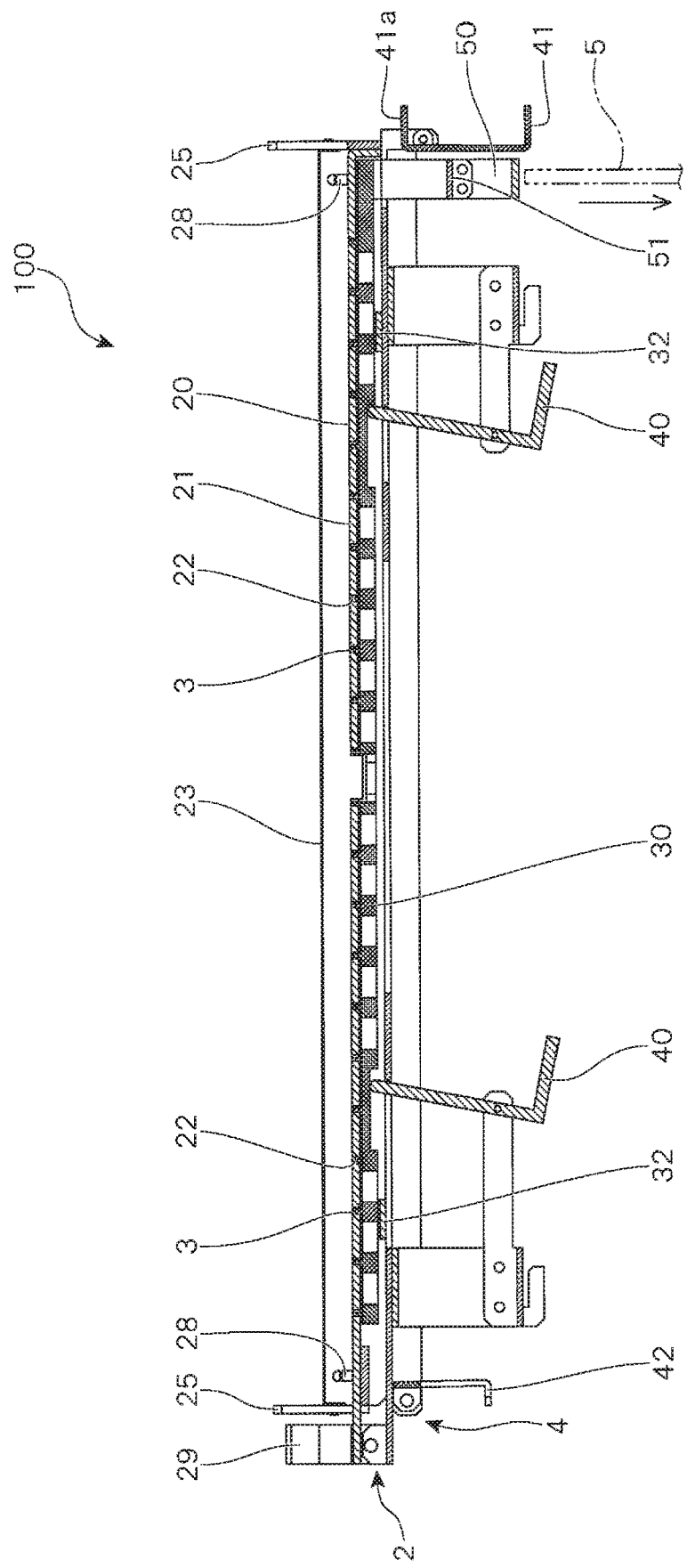
FIG. 9 is an explanatory view for explaining the operation of the cell culture apparatus shown in FIG. 3.

After allowing the base 2 to move rotatably by a predetermined angle, the push-up member 5 is moved downward. As a result, as shown in FIG. 9, the base 2 is rotatably moved downward and returns to the initial position. At this time, vibration is transmitted to the container 1 held on the mounting surface 20 of the base 2 by the impact generated by receiving of the base 2 by the supporting frame 4. Due to such a configuration, by repeating the rotating operation of the base 2 by moving the push-up member 5 up and down, an operation in which after allowing the container 1 to be moved to a position higher than the initial position, returning the container 1 to the initial position and applying vibration to the container 1 that has returned to the initial position are repeated, whereby the content liquid of the container 1 can be stirred.

As shown in FIG. 10, for example, a driving mechanism for moving the push-up member 5 up and down can be configured as a cam mechanism includes a plate cam 5*b* having a first cam surface 5*c* with an arcuate contour and a second cam surface 5*d* with a linear contour, and a receiving plate 5*a* provided horizontally at the base end of the push-up member 5 as a follower. The configuration of the driving mechanism is not limited thereto.

In the example shown in FIGS. 10A to 10H, the curvature of the cam surfaces 5*c* and 5*d*, the position of a drive shaft 5*e* for rotating the plate cam 5*b*, and the rotational speed of the drive shaft 5*e* are appropriately set so that the push-up member 5 moves upward as the first cam surface 5*c* pushes up a receiving plate 5*a* (see FIGS. 10A to 10E), the plate cam 5*b* leaves from the receiving plate 5*a* when switching to the second cam surface 5*d*, and then the push-up member 5 falls down (see FIGS. 10F to 10H), whereby the up-and-down movement of the push-up member 5 is repeated as the plate cam 5*b* rotates in a fixed direction. When the driving mechanism is configured as described above, when the base 2 rotates downward to return to its initial position, the base 2 rotatably moves as if it falls down, so that an impact is generated when the supporting frame 4 receives the base 2.

After the rotational operation of the base 2 is repeated several times to sufficiently stir the content liquid of the container 1, the culture medium M is additionally supplied to the container 1. At this time, since the engagement of the hooks 41 and 42 is released, the pressing plate 23 is pushed up by the container 1 of which the amount of the content is increased to have an increased thickness. When the pin 26 projecting from the pressing plate 23 reaches the upper edge of the guide hole 24, the pressing plate 23 cannot move upward anymore and is fixed at the upper position (see FIG. 12). This makes it possible to increase the pressure inside of the container 1 of which the amount of the content has been increased by additional supply of the culture medium M, and even in the expansion culture step, by allowing the inside of the container to be in a pressurized state, it is possible to prevent the cells C from being damaged by excessive flow of the content liquid and to effectively prevent the gas dissolved in the medium M from becoming bubbles and staying in the container.

By operating the culture apparatus 100 as described above, shift to the expansion culture step is completed, and thereafter, the culture of the cells C is continued until the predetermined cell density is reached.

As described above, the culture apparatus 100 can be shifted from the curing culture step to the expansion culture step by the rotational operation of the base 2. In the expansion culture step, the bottom surface of the container 1 that becomes flat by being flattened by the weight of the content liquid is used as a culture surface. If the bottom surface of the container 1 is not sufficiently flattened, wrinkles or slacks are generated on the culture surface, and cells are accumulated in that portion, resulting in excessive cell density. Further, since movement of cells is restricted, it may be concerned that proliferation efficiency of cells is lowered.

In addition, such a place where cells are accumulated may cause cells to remain in the container when recovering cultured cells.

In Patent Document 4, a method is taken in which holes are bored at the four corners of the culture container and fixtures are provided vertically at the four corners of the container mounting table, and the holes of the culture container are engaged with the fixtures of the container mounting table and the culture container is pulled, the culture surface is flattened.

However, this method is insufficient to eliminate disadvantages that, in a state where a culture solution is placed in the culture container, wrinkles or slacks are generated on the culture surface of the culture container, and a place where cells are accumulated is formed, the proliferation efficiency of cells is lowered.

Figure 17:
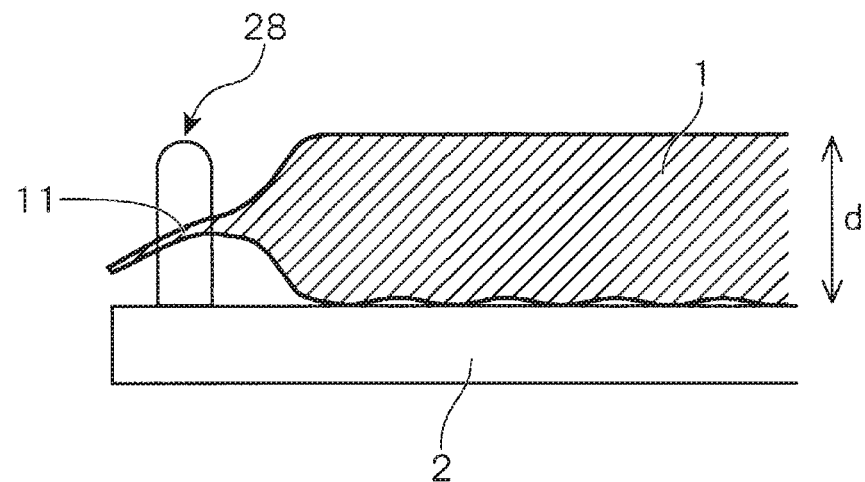
FIG. 17 is an explanatory view showing a state in which a hole formed in the container is engaged with a fixture.

Specifically, FIG. 17 shows an example in which the hole 11 provided in the container 1 is engaged with the fixture 28 to pull the container 1. This method is still insufficient to avoid generation of wrinkles or slacks on the bottom surface of the container 1.

In the present embodiment, as mentioned above, when attaching the container 1 to the culture apparatus 100, holes 11 bored at the four corners of the container 1 are engaged with fixtures 28 provided at the four corners of the base 2. At this time, it is preferred that a recess 28*a* be provided in the fixture 28 and the hole 11 provided in the container 1 be engaged with the recess 28*a* so that the end part of the container 1 is held at the height of the recess 28*a*. By doing so, when transferring to the expansion culture step, the bottom surface of the container 1 can be flattened easily by the weight of the content liquid, whereby the bottom surface of the container 1 can be sufficiently flat.

In such embodiment, the arrangement and number of the fixtures 28 are not particularly limited, and it suffices that two or more fixtures 28 be oppositely arranged on the periphery of the base 2. In the case of using a common container 1, it is preferable that the fixture 28 be provided vertically at the four corners of the base 2, and that in the case of using a container 1 having a relatively large size, a larger number of fixtures 28 be provided vertically. In addition, the fixture 28 can be arranged such that one fixture is disposed in the middle of the end part of each of the shorter sides of the base 2, or alternatively, one fixture is disposed in the middle of the end part of one of the shorter sides and two or more fixtures are disposed at the opposing end parts of one of the short sides.

On the other hand, the hole 11 bored in the container 1 can be provided in accordance with the arrangement and number of the fixture 28 provided in the base 2, and in order to allow the peripheral part of the hole 11 to be engaged with the recess 28*a* by inserting the fixture 28 into the hole 11, the hole 11 can be provided at a heat-sealed end part region, etc. That is, it suffices that two or more holes 11 be provided at the end part of the container 1 in correspondence with two or more fixtures 28 provided at the peripheral part of the base 2. At this time, it is needless to say that sealing property of the container 1 is required to be prevented from being lowered by provision of the holes 11 in the container 1.

The shape of the fixture 28 is not particularly limited. For example, it may be substantially columnar, but other shapes such as a substantially rectangular parallelepiped shape may be used. Further, the upper part of the recess 28*a* may be formed in a dome shape, and the lower part of the recess 28*a* may be formed into a columnar shape or a prismatic shape.

It is preferable that the recess 28*a* be formed circumferentially with respect to the horizontal plane in the fixture 28, but the manner of formation is not limited thereto, and it may be formed in a semi-circumferential shape, an arc shape or the like with respect to the horizontal plane in the outer direction of the base 2. Further, the horizontal cross section of the recess 28a is not limited to a circular shape, and it may be a polygonal shape, a star shape, or the like.

The position where the recess 28a is formed in the fixture 28 is determined based on the thickness of the container 1 that becomes full by filling the culture solution in the culture container 1 to a full capacity thereof taking into consideration the thickness of the container 1 at the time of being full.

Figure 15:
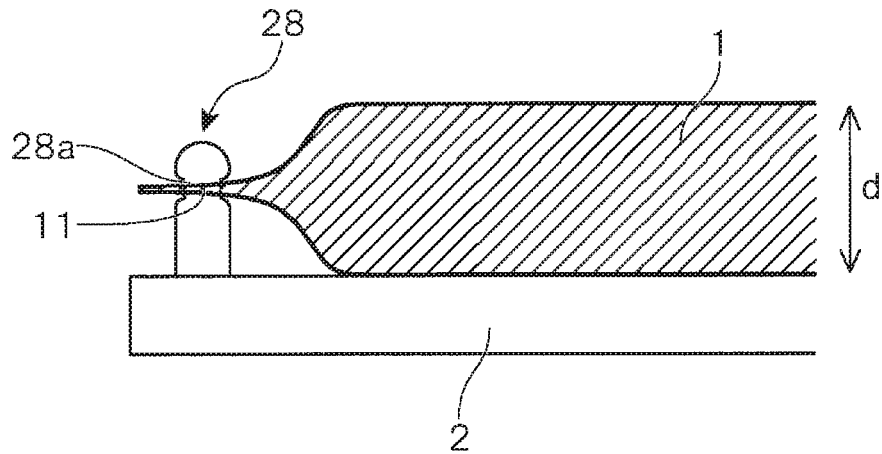
FIG. 15 is an explanatory view showing one example in which a hole formed in the container is engaged with a recess formed in a fixture.

FIG. 15 shows a state in which, in the fixture 28, the recess 28a is formed at a position, upward from the surface of the base 2, ½ of the thickness of the container 1 which is full (almost ½ of the liquid depth d), and the peripheral edge portion of the hole 11 of the container 1 is engaged with the recess 28a.

Due to such a configuration, the end part of the container 1 is held at the height of the recess 28a, and the container 1 can be fixed to the base 2 with the bottom surface of the container 1 being flattened.

Figure 16:
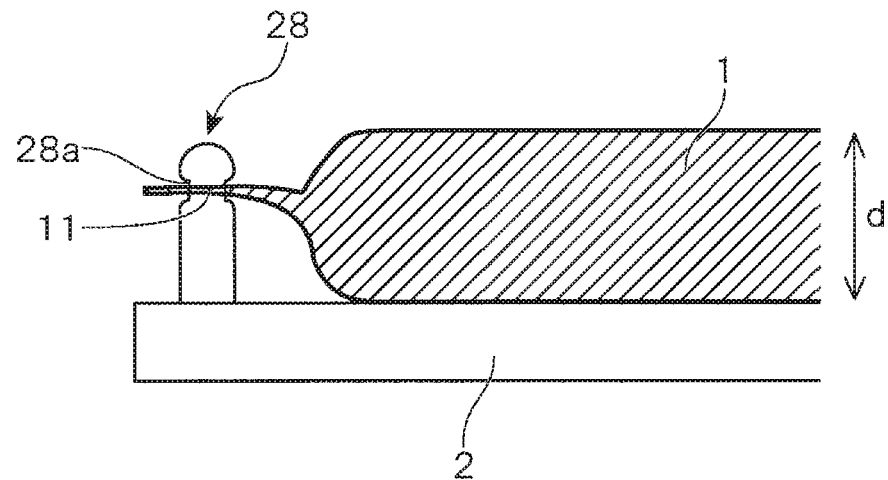
FIG. 16 is an explanatory view showing another example in which a hole formed in the container is engaged with a recess formed in a fixture.

FIG. 16 shows a state in which, in the fixture 28, the recess 28a is formed at a position, upward from the surface of the base 2, ¾ of the thickness of the container 1 which is full (almost ¾ of the liquid depth d) and the peripheral edge portion of the hole 11 of the container 1 is engaged with the recess 28a.

Due to such a configuration, by pulling up the opposing end parts in the container 1 to a height of the recess 28a, the bottom surface of the container 1 can be flattened. Such advantageous effects can be similarly obtained if the recess 28a is at a position upward from the surface of the base 2 that is slightly higher than the thickness of the container 1 that is full.

From such a viewpoint, it is preferable that a position where the recess 28a is formed in the fixture 28 be set, upward from the surface of the base 2, such that it corresponds to ½ to ⅔, more preferably ½ to 1, further preferably ½ to ¾, of the thickness of the container 1 which is full.

By allowing the position at which the recess 28a is formed in the fixture 28 to be in the above-mentioned range, the bottom surface of the container 1 after the culture step is shifted to the expansion culture step can be kept in a flattened state more reliably, and the culture surface can be in a state where no wrinkles or slacks are formed. As a result, the culture area of the container 1 can be maximized.

Further, by flattening the bottom surface of the container 1 more reliably, cells can be uniformly distributed (dispersed) in the container 1. Therefore, it is possible to optimize the culture conditions in cell culture, and it is possible to further improve the cell proliferation efficiency.

Hereinabove, the present invention was explained while referring to preferable embodiments. The present invention is not restricted to the above-mentioned embodiments, and it is needless to say that various modifications are possible within the scope of the present invention.

For example, in the above-mentioned embodiments, the bottom surface of the container 1 is partially raised and separated into plural compartments 10 by holding the container 1 on the base 2 in which the partition pieces 3 that can be protruded from the mounting surface 20 for a prescribed height are embedded in a state that the partition pieces 3 are protruded. The cell culture method according to the present invention can be implemented without being limited thereto.

As long as the bottom surface of the container 1 can be partially raised and separated into plural compartments 10 by utilizing the deformation of the container 1 formed of a flexible material, for example, a plurality of rod-like members may be arranged side by side on the mounting surface 20, and the container 1 is held thereon.

Even in that case, the bottom surface of the container 1 is partially raised by pushing up by the rod-like member, and as a result, the bottom surface is separated into plural compartments 10. If such rod-like members are drawn, the bottom surface of the container 1 is flattened by the weight of the content liquid, whereby the culture area of the container is expanded.

In the above-mentioned embodiment, the pressing plate 23 is attached by providing vertically annular rising sections 25 forming an elongated hole-shaped guide hole 24 at the four sides of the base 2, and inserting the pin 26 that is horizontally projected at the four corners of the pressing plate 23. The manner of attachment of the pressing plate 23 is not limited thereto. It suffices that the pressing plate 23 be attached such that it can be moved vertically in accordance with the amount of the content of the container 1. For example, it can be attached as shown in FIG. 13 and FIG. 14.

Figure 13:
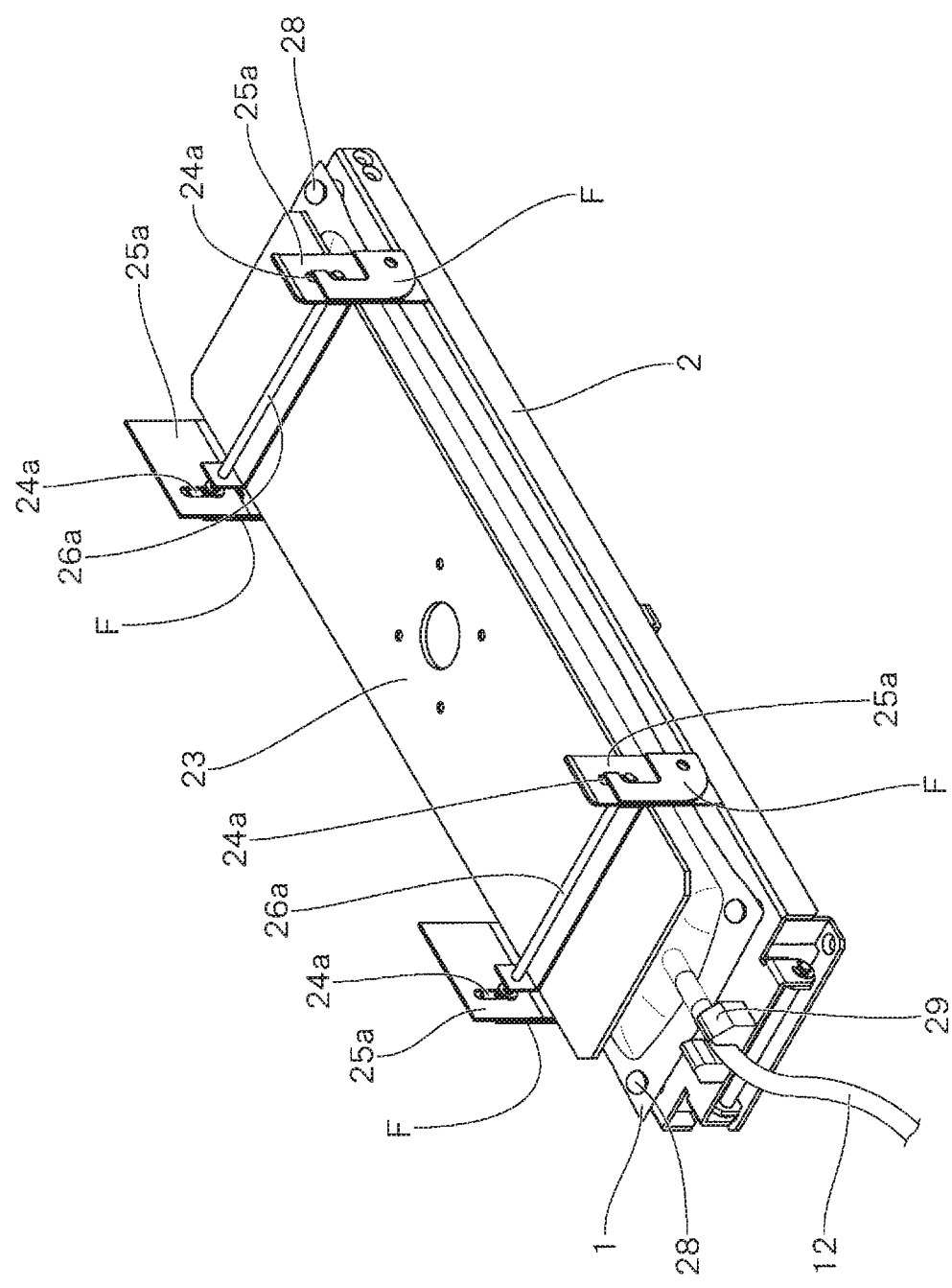
FIG. 13 is a perspective view showing an outline of a modification example of the cell culture apparatus according to the embodiment of the present invention.
Figure 14:
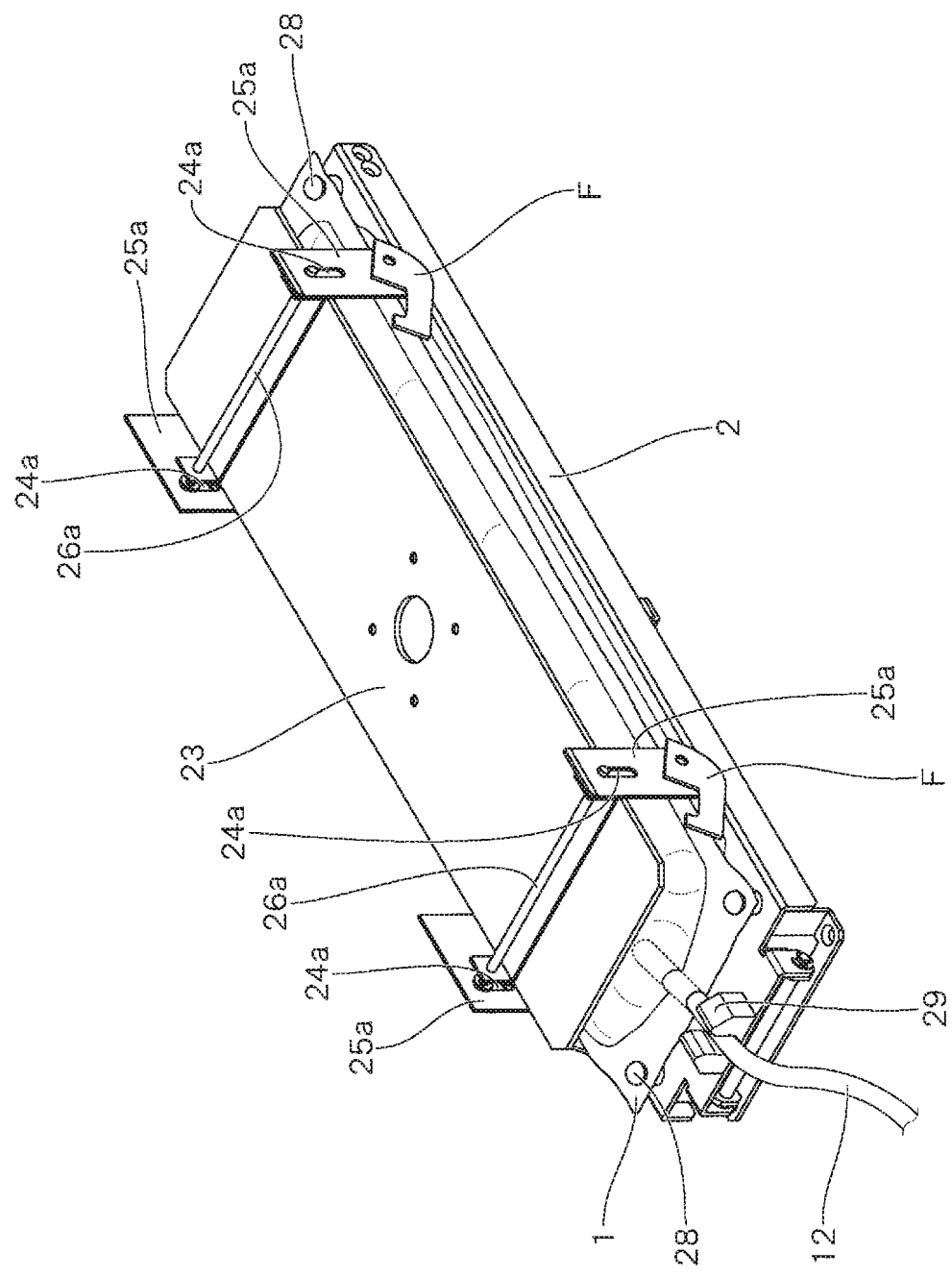
FIG. 14 is a perspective view showing an outline of a modification example of the cell culture apparatus according to the embodiment of the present invention.

In FIG. 13 and FIG. 14, two pairs of rising sections 25a having elongated hole-shaped guide holes 24a are provided vertically at opposing positions on the longer sides of the base 2 so as to form a pair, and the pressing plate 23 is attached so that it can be moved up and down through a supporting rod 26a disposed between each of the rising sections 25a forming a pair. In the curing culture step, the hook F is engaged with the supporting rod 26a inserted into the guide hole 24a to suppress the upward movement of the pressing plate 23, whereby the upper surface of the container 1 in which a content is filled in a prescribed amount is pressed by the pressing plate 23 fixed at a lower position, thus enabling the inside of the container to be pressurized (see FIG. 13).

In the expansion culture step, by releasing the engagement of the hook F, the pressing plate 23 can be moved upward. When the supporting rod 26a reaches the upper edge of the guide hole 24a, the pressing plate 23 cannot be moved to a position higher than the upper edge, and fixed at an upper position. Due to such a configuration, the upper surface of the container 1 of which the content amount is increased to have an increased thickness by additional supply of a culture medium M is pressed by the pressing plate 23, thus enabling the inside of the container to be pressurized (see FIG. 14).

In order to release the engagement of the hook F, when the base 2 is rotatably moved in the same manner as in the above-mentioned embodiment, the hook F is allowed to move rotatably by its own weight by the inclination of the base 2.

The documents described in the specification and the specification of Japanese application(s) on the basis of which the present application claims Paris convention priority are incorporated herein by reference in its entirety.

INDUSTRIAL APPLICABILITY

The present invention can be preferably used in gene therapy, immunotherapy, regenerative therapy, production of antibody medicines, etc. where cells are cultured aseptically and easily in a closed system by using a cell culture apparatus.

DESCRIPTION OF NUMERICAL SYMBOLS

1 Container
10 Compartment

11 Hole
2 Base
20 Mounting surface
23 Pressing plate
24 Guide hole
25 Annular rising piece
26 Pin
28 Fixture
28a Recess
3 Partition piece
4 Supporting frame
41,42 Hook
C Cells
M Culture medium

The invention claimed is:

1. A cell culture apparatus for conducting cell culture comprising:
a container formed of a flexible material and adapted for receiving a culture medium including cells,
a base having a flat mounting surface that holds the container; and
partition pieces that can be protruded from the mounting surface for a prescribed height for partially raising a bottom surface of the container and are embedded in the base,
wherein the base is provided with a holding member that forms the mounting surface and a partition plate on which a plurality of the partition pieces is arranged,
wherein when the partition pieces are accommodated into the base, upper end surfaces of the partition pieces are flush with the mounting surface.

2. The cell culture apparatus according to claim 1, wherein the plurality of the partition pieces is arranged in parallel with each other with a prescribed interval.

3. The cell culture apparatus according to claim 1, wherein the base is pivotably supported at one end thereof by a supporting frame such that it can be rotatably moved and due to the rotational operation of the base, after the container is moved to a position higher than the initial position, the container is returned to an initial position by rotatably moving the base as if it falls down and vibration that is due to an impact generated by receiving of the base by the supporting frame is applied to the container returned to the initial position, thereby to stir a content liquid in the container.

4. The cell culture apparatus according to claim 1, wherein a pressing plate for pressurizing an inside of the container by pressing the container held on the mounting surface is attached such that it can be moved up and down in accordance with an amount of a content in the container.

5. The cell culture apparatus according to claim 4, wherein annular rising pieces each having an elongated guide hole are vertically provided at each of four corners of the base, and by inserting a pin provided at each of the four corners of the pressing plate into the guide hole, the pressing plate is attached to the base such that it can be moved up and down, and a hook that is engaged with the pressing plate and fixes the pressing plate at a prescribed position is provided.

6. The cell culture apparatus according to claim 5, wherein the base is pivotably supported by a supporting frame such that the base can be rotatably moved, and due to the rotational operation of the base, the engagement of the hook is released.

7. The cell culture apparatus according to claim 1, wherein two or more fixtures that fix the container are vertically provided such that they oppose each other on a periphery of the base, and a recess is formed in each of the two or more fixtures.

8. The cell culture apparatus according to claim 7, wherein the recess is formed in each of the two or more fixtures at a position, upwardly from the surface of the base, corresponding to $\frac{1}{2}$ to $\frac{3}{2}$ of a thickness of the container when the container is filled to capacity.

9. The cell culture apparatus according to claim 7, wherein the recess is formed in each of the two or more fixtures circumferentially relative to the horizontal plane.

10. The cell culture apparatus according to claim 7, wherein each of the two or more fixtures is provided vertically at each of corners of the base.

11. The cell culture apparatus according to claim 7, wherein two or more holes are provided at end parts of the container such that they correspond to any of the two or more fixtures, and any of the two or more fixtures are inserted into the holes to allow peripheral parts of the holes to be engaged with the recess.

* * * * *